US00PP19778P2

(12) United States Plant Patent
van Rysselberghe

(10) Patent No.: US PP19,778 P2
(45) Date of Patent: Feb. 24, 2009

(54) ***PHALAENOPIS* PLANT NAMED 'IKARIA'**

(50) Latin Name: *Phalaenopis*
Varietal Denomination: Ikaria

(75) Inventor: Ronie van Rysselberghe, Lochristi (BE)

(73) Assignee: Microflor NV, Lochristi (BE)

( * ) Notice: Subject to any disclaimer, the term of this patent is extended or adjusted under 35 U.S.C. 154(b) by 0 days.

(21) Appl. No.: 12/011,443

(22) Filed: Jan. 25, 2008

Related U.S. Application Data

(60) Provisional application No. 60/921,480, filed on May 11, 2007.

(51) Int. Cl.
*A01H 5/00* (2006.01)

(52) U.S. Cl. ..... Plt./311

(58) Field of Classification Search ..... Plt./311
See application file for complete search history.

*Primary Examiner*—Annette H Para

(57) ABSTRACT

A new cultivar of *Phalaenopsis* plant named 'Ikaria' that is characterized by a large overall size, large green leaves and flowers that have white petals with white to yellow and red hips.

1 Drawing Sheet

Botanical classification: *Phalaenopsis.*
Variety denomination: 'Ikaria'.

Cross Reference to Related and Co-Pending Applications

This patent application claims priority to U.S. Provisional patent application Ser. No. 60/921,480, filed on May. 11, 2007. The entire contents of which are herein incorporated by reference.

BACKGROUND OF THE INVENTION

The present invention relates to a new and distinct cultivar of *Phalaenopsis* plant botanically known as *Phalaenopsis* and hereinafter referred to by the cultivar name 'Ikaria'.

The new cultivar is the product of a breeding program conducted by the inventor in a cultivated area of Lochristi, Belgium.

'Ikaria' is a hybrid that originated from the hybridization of the female or seed parent a proprietary *Phalaenopsis* identified as 'PHMFW232 (not patented) and the male or pollen parent a proprietary *Phalaenopsis* identified as 'PHMFW064' (not patented). The cultivar 'Ikaria' was selected by the inventor in September of 2000 as a single plant within the progeny of the stated cross in Lochristi, Belgium.

Asexual reproduction by tissue culture of the new cultivar 'Ikaria' was first performed in October of 2000 in Lochristi, Belgium. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Phalaenopsis* cultivar 'Ikaria'. These traits in combination distinguish 'Ikaria' as a new and distinct cultivar.

1. *Phalaenopsis* 'Ikaria' exhibits a large overall size.
2. *Phalaenopsis* 'Ikaria' exhibits flowers that have white petals with white to yellow and red hips.
3. *Phalaenopsis* 'Ikaria' exhibits large, green leaves.

The new cultivar 'Ikaria' is distinguishable from the female parent *Phalaenopsis* 'PHMFW232' by the following characteristics:

1. 'Ikaria' has larger flowers.

The new cultivar ;Ikaria' is distinguishable from the male parent *Phalaenopsis* 'PHMFW064' by the following characteristics:

1. 'Ikaria' has larger flowers.

The closest comparison cultivar is *Phalaenopsis* 'Saloniki'. The new cultivar *Phalaenopsis* 'Ikaria' differs from 'Saloniki' not patented by the following characteristics:

1. 'Ikaria' has larger flowers.
2. 'Saloniki' has a larger number of branches than 'Ikaria'.

BRIEF DESCRIPTION OF THE DRAWING

The accompanying photograph illustrates the distinguishing traits of *Phalaenopsis* 'Ikaria'. The plant in the photograph shows an overall view of an 18 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Phalaenopsis* cultivar named 'Ikaria'. Data was collected in Lochristi, Belgium from 18 month old greenhouse grown plants in 12 centimeter containers. The time of year was Fall. The average temperature during the first 25 weeks was 26° Centigrade. The average temperature during the next 4 weeks was 18° Centigrade. The average temperature during the last weeks was 20° Centigrade.

The light level was natural outdoor light and there were no photoperiodic treatments or growth retardants used. Color determinations are in accordance with the Royal Horticultural Society Colour Chart 2001 edition, except where general color terms of ordinary dictionary significance are used. The growing requirements are similar to the species. 'Ikaria' has not been tested under all possible conditions and phenotypic differences may be observed with variations in environmental, climatic, and cultural conditions, however, without any variance in genotype.

Botanical classification: *Phalaenopsis* 'Ikaria'.
Parentage: 'Ikaria' is a hybrid plant that resulted from the hybridization of the following parent plants:
*Female parent.*—*Phalaenopsis* 'JPH00150'.
*Male parent.*—*Phalaenopsis* 'JPH00423'.
Vigor: Moderate.
Growth rate: Moderate.
Growth habit: Upright.
Plant shape: Monopodial with basal rosette and flowering stems growing from a basal rosette.
Suitable container size: 12 cm container.
Height to top of flowers: Average 53.7 cm. in height.
Height to top of leaves: Average 11.9 cm. in height.
Width: Average 31.8 cm. in width.
Hardiness: USDA Zone 11.
Propagation: Tissue culture.
Time to initiate roots summer: Approximately 63–70 days to produce roots on an initial cutting at 26–28° Centigrade.
Time to initiate roots winter: Approximately 70–77 days to produce roots on an initial cutting at 26–28° Centigrade.
Time to produce a rooted cutting or liner summer: Approximately 140–175 days at 26–28° Centigrade.
Time to produce a rooted cutting or liner winter: Approximately 154–189 days at 26–28° Centigrade.
Root system: Fleshy, rounded, slightly glossy, average diameter 5 mm.
Foliage:
*Texture.*—Smooth, glossy, slightly furrowed.
*Leaf arrangement.*—Distichous
*Quantity of leaves per plant.*—6.
*Leaf shape.*—Obovate.
*Leaf apex.*—Unequal Acute.
*Leaf base.*—Cuneate.
*Leaf length.*—Average 19.0 cm. in length.
*Leaf width.*—Average 8.4 cm. in width.
*Pubescence.*—Absent.
*Leaf margin.*—Entire.
*Vein pattern.*—Camptodromous.
*Young leaf color* (*upper surface*).—Varies from 137A to 146A to 146B.
*Young leaf color* (*lower surface*).—Between 146A and 146B.
*Mature leaf color* (*upper surface*).—Varies from 137A to 146A.
*Mature leaf color* (*lower surface*).—146A to 146B.
*Vein color* (*lower surface*).—Varies from 137B to 146A.
*Vein color* (*upper surface*).—146A to 146B.
*Durability of foliage to stress.*—High.
Flower:
*Flower arrangement.*—Axillary raceme.
*Inflorescence type.*—Raceme.
*Inflorescence dimensions.*—Average 18.9 cm. in diameter and 49.1 cm. in length.
*Flowering habit.*—Once a year.
*Flower form.*—Zygomorphic.
*Quantity of flowers per inflorescence..*—Average 8.
*Quantity of flower stems per plant.*—Average 2.
*Quantity of flowers and buds per plant.*—Average 16.
*Flowering season.*—Late fall to spring.
*Time to flower or response time.*—6 months.
*Rate of flower opening.*—Lowest flowers of the raceme open first, all flowers will open in approximately 4 weeks.
*Fragrance.*—None.
*Self-cleaning or persistent.*—Self-cleaning.
*Flower bud length.*—2.2 cm. in length.
*Flower bud diameter.*—1.9 mm. in diameter.
*Flower bud shape.*—Broad ovate.
*Bud color.*—145C tinged with 176C to 176D.
*Rate of bud opening.*—14 days.
*Flower aspect.*—Outward.
*Flower shape.*—Zygomorphic.
*Vertical flower dimensions.*—9.7 cm.
*Horizontal flower dimensions.*—10.6 cm.
*Flower depth.*—3.2 cm.
*Flower longevity.*—Over 28 days.
*Petal appearance.*—Dull.
*Petal texture.*—Glabrous.
*Petal arrangement.*—One petal one each side of the column.
*Number of petals.*—Two in number.
*Petals fused or unfused.*—Unfused.
*Petal shape.*—Reniform.
*Petal margin.*—Entire.
*Petal apex.*—Rounded.
*Petal dimensions.*—5.1 cm. in length and 6.6 cm. in width.
*Petal color when opening* (*upper side*).—N155A.
*Petal color when opening* (*under side*).—N155A; tinged with 157D.
*Petal color when fully opened* (*upper side*).—N155A.
*Petal color when fully opened* (*under side*).—N155A.
*Petal color fading to.*—Not fading.
*Labellum appearance.*—Glabrous, dull.
*Labellum arrangement.*—Three-lobed.
*Labellum shape.*—Lobed, outward lobes broad obovate, middle lobe deltoid.
*Labellum tip.*—Cleft into two curled, linear projections curled backwards.
*Labellum dimensions.*—Average 3.3 cm. in length and 2.6 cm. in width.
*Labellum color, young, upper side.*—N155A; lower margin of lateral lobes and base of central lobe 4A to 5B; base of each lobe striped 71A. Callosities 10B to 10C, dotted 71A. Projections 4A to 4B.
*Labellum color, young, lower side.*—N155A; lower margin of lateral lobes and central lobe 5B; base each of each lobe 75A to 75B.
*Labellum color, mature, upper side.*—N155A; lower margin of lateral lobes and base of central lobe 5A; base of each lobe striped 71A. Callosities 10A to 10B, dotted 71A. Projection 4A to 4B.
*Labellum color, mature, lower side.*—N155A; lower margin of lateral lobes and base of central lobe 5B; base of each lobe 75A to 75B.
Callosities:
*Callositie location.*—At the base of the central lobe of the labellum and between the lateral lobes.
*Callositie dimensions.*—Average 6 mm in length and 3 mm in width (per callosity).
Sepals:
*Sepal appearance.*—Dull, smooth.
*Sepal arrangement.*—Two lateral sepals and one dorsal sepal.
*Number of sepals.*—Three in number.
*Sepal shape.*—Broad elliptic.

*Sepal margin.*—Entire.
*Sepal tip.*—Rounded.
*Sepal base.*—Cunuate.
*Lateral sepal length.*—Average 5.2 cm.
*Dorsal sepal length.*—Average 5.2 cm.
*Lateral sepal width.*—Average 3.4 cm.
*Dorsal sepal width.*—Average 3.6 cm.
*Lateral sepal color, immature, upper surface.*—N155A, tinged 157B to 157C near the base. Dorsal sepal N155A; slightly tinged 157D near the base.
*Dorsal sepal color, immature, upper surface.*—145C to 145D. Margins 157D, tips slightly tinged 77C. Dorsal sepal 145C to 145D.
*Lateral sepal color, immature, under surface.*—N155A, only very slightly tinged 157D near the base. Dorsal sepal N155A.
*Dorsal sepal color, immature, under surface.*—N78B.
*Lateral sepal color, mature, upper surface.*—N157A, margins N155A. Tips slightly tinged 77C. Dorsal sepal 157D, tinged 77D.

Peduncle:
*Peduncle dimensions.*—Average 38.5 cm. in length and 5 mm. in diameter.
*Peduncle angle.*—20° from vertical.
*Peduncle color.*—Between 148A, dotted lighter 148D.
*Peduncle strength.*—Strong.

Pedicels:
*Pedicel dimensions.*—Average 4.7 cm. in length and 3.5 mm. in diameter.
*Pedicel angle.*—75° from vertical.
*Pedicel color.*—146C to 146D.
*Pedicel strength.*—Moderate to strong.

Reproduction organs:
*Column dimensions.*—Average 9 mm in length and 6 mm in width.
*Column color.*—N155A.
*Pollinia quantity.*—Moderate.
*Pollinia diameter.*—1.5 mm.
*Pollinia color.*—23A to 24A.
*Stigma shape.*—Rounded concave.
*Stigma color.*—N155A.
*Stigma dimensions.*—5 mm in length and 5 mm in width.
*Ovary color.*—65C to 656D.
*Ovary dimensions.*—9 mm in length and 2.5 mm in diameter.

Seed: Seed production has not been observed.

Disease resistance: Plants of the new *Phalaenopsis* are resistant to root diseases.

Pest resistance: Plants of the new *Phalaenopsis* have not been observed for pest resistance.

It is claimed:

1. A new and distinct variety of *Phalaenopsis* plant named 'Ikaria' as described and illustrated.

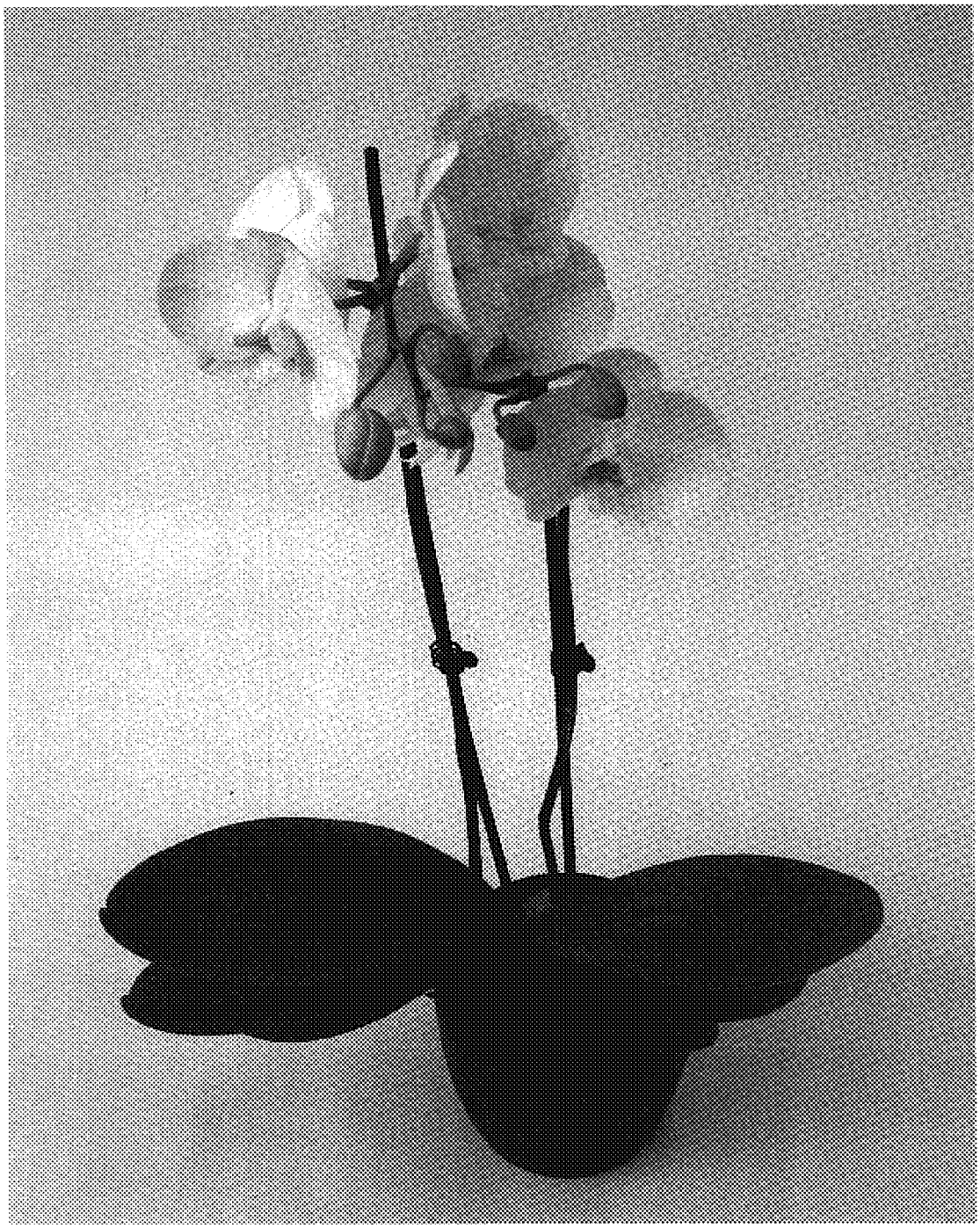

* * * * *